United States Patent [19]

Schwab

[11] Patent Number: 4,520,360
[45] Date of Patent: May 28, 1985

[54] SENSING VERTICAL AND HORIZONTAL VISIBILITY

[75] Inventor: Carl E. Schwab, Huntington Station, N.Y.

[73] Assignee: General Signal Corporation, Stamford, Conn.

[21] Appl. No.: 419,885

[22] Filed: Sep. 20, 1982

[51] Int. Cl.³ .............................................. G08G 5/00
[52] U.S. Cl. .................................. 340/947; 73/170 R; 356/4
[58] Field of Search ............. 73/170 R; 340/945, 947, 340/952, 870.28, 870.29; 356/4, 5, 11, 1, 437, 438; 324/207

[56] References Cited

U.S. PATENT DOCUMENTS

| | | | |
|---|---|---|---|
| Re. 21,838 | 6/1941 | Buckley | 340/947 |
| 3,299,769 | 1/1967 | Byers | 340/952 |
| 3,406,387 | 10/1968 | Werme | . |
| 3,963,347 | 6/1976 | Segre | 356/4 |
| 4,288,158 | 9/1981 | Frungel | 356/4 |
| 4,289,397 | 9/1981 | Itzkan | 356/4 |
| 4,295,139 | 10/1981 | Arpino | 340/949 |
| 4,318,076 | 3/1982 | Whitfield | 340/947 |
| 4,369,425 | 1/1983 | Andersen | 340/945 |
| 4,403,862 | 9/1983 | Lofgren | 356/437 |
| 4,419,731 | 12/1983 | Puffett | 356/4 |
| 4,422,041 | 12/1983 | Lienau | 324/207 |

OTHER PUBLICATIONS

Skopograph, brochure by Impulsphysik GmbH.
Laser-Ceilograph, brochure by Impulsphysik GmbH.

*Primary Examiner*—James J. Groody
*Assistant Examiner*—Michael F. Heim
*Attorney, Agent, or Firm*—Pollock, Vande Sande & Priddy

[57] ABSTRACT

Unattended measurements of horizontal and vertical visibility are broadcast, along with the results of time trend analysis so as to provide for short-term prediction of visibility. A calibration mechanism is provided along with sensors to determine mis-alignment of the apparatus. Broadcast information is particularly useful to pilots approaching unattended airports for landing.

14 Claims, 9 Drawing Figures

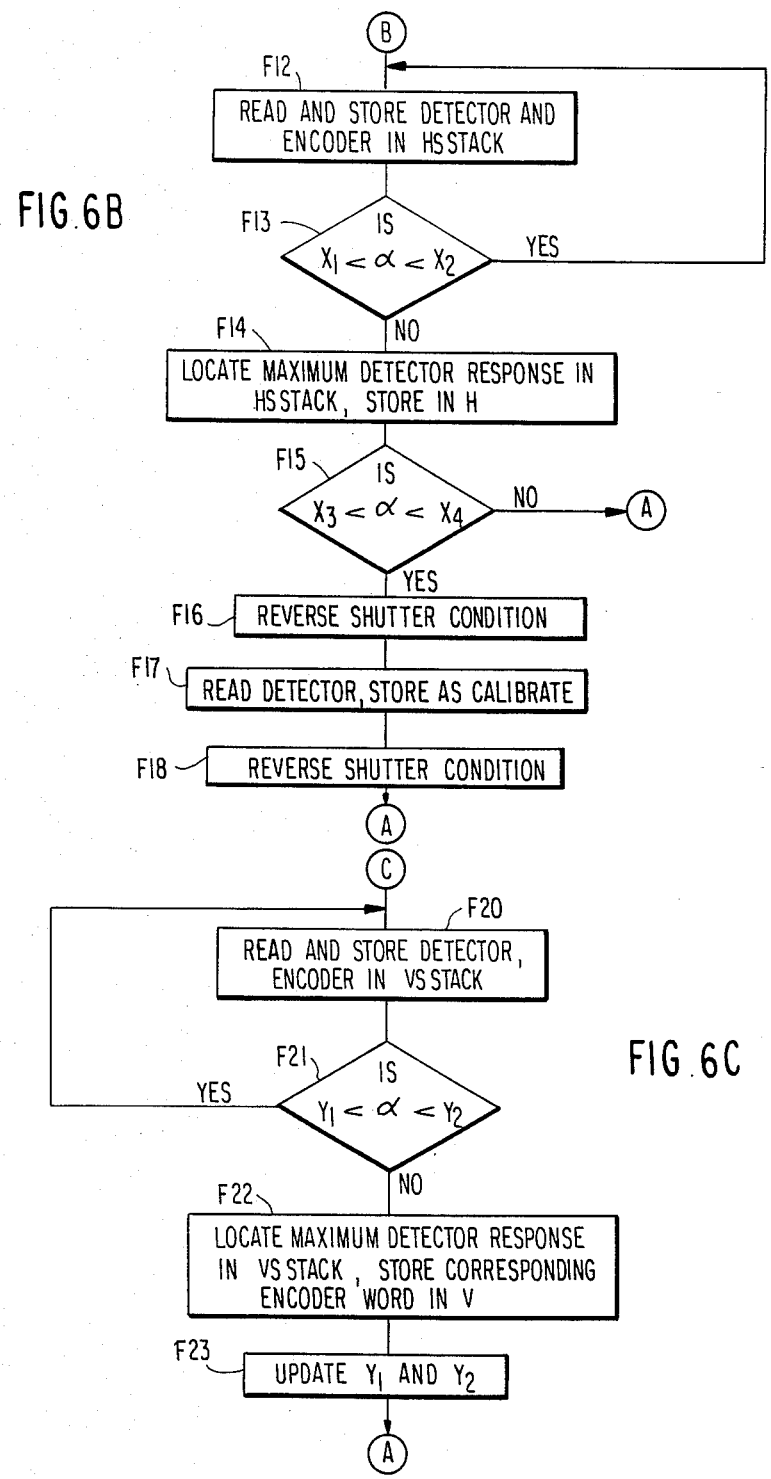

SENSING VERTICAL AND HORIZONTAL VISIBILITY

DESCRIPTION

1. Field of the Invention

The present invention relates to information sensing devices which are particularly useful at airports for measuring airport related parameters such as horizontal and vertical visibility.

2. Background Art

It is well known to those skilled in the art that airport operations, and the regulations which govern those operations require that an aircraft pilot not attempt a landing unless vertical and horizontal visibility at the airport exceed certain predetermined minimums. Typically, the pilot starts an approach and then at some specific indicated altitude the pilot must determine if he has sufficient visibility to continue the procedure or to abort the attempt. To provide the pilot with information, a variety of instruments are available. Typically, a human being will monitor the instruments and input the desired information into some type of apparatus for transfer to the pilots of approaching aircraft. That information transfer apparatus may simply be a radio to implement a voice message. Alternatives include the use of prerecorded announcements which are either automatically broadcast or broadcast on demand to approaching aircraft.

Although in theory these measurements, and the transfer of information to the pilot could be automated, up to the present time that automation has not been effected for a number of reasons. The use of a human to monitor the instruments provides some protection against instrument failure, i.e. the human monitor will obviously be capable of detecting certain failures of the sensing equipment and taking appropriate action. In addition, while the regulations govern the conditions under which an attempted landing can be made, information is typically transmitted to the pilot sometime before the landing is attempted. Because of this, the pilot wants to know, in addition to information describing present conditions, the conditions that can be predicted for his actual arrival time. For example, if conditions at the present time are above minimums, but are decreasing such that it can be readily predicted by the time the pilot arrives, the conditions will be below minimums, then if the pilot receives the appropriate prediction, he can attempt to alter his course for a location where acceptable landing conditions are more likely.

As the use of commuter and non-commercial aircraft expands (both personal and business use), aircraft operations at smaller and less congested airports increase. Smaller airports have a number of characteristics which typically differ from the larger airports used by commercial aircraft. For one thing, the equipment located at these smaller airports is typically simpler, and generally less expensive. Furthermore, it is not at all unusual for the smaller airports to be unattended, or at least unattended for a large portion of the time during which aircraft operations may take place.

The ability of the eye to perceive objects through the atmosphere is fundamentally limited by the presence of airborne particles. These particles may be moisture, ice, sand, dust, etc. The visibility reduction occurs because of reflective loss or absorptive loss. Reflective losses are relatable to scatter coefficients and absorptive losses are relatable to extinction coefficients.

Present day equipments exist that are capable of measuring forward scatter, backscatter and extinction coefficients with repeatable results. These coefficients are useable to predict horizontal visibility, i.e. in a horizontal plane at the level where they are measured. Present equipments allow measurement of cloud base heights and fluctuations as a function of time. These measurements are used to define the vertical visibility. Presently, the horizontal and vertical visibility measurements are performed separately and require human intervention for correlation and interpretation.

Impulsphysik GMBH (Hamburg), for example, markets a Laser-Ceilograph LD-WHL for measuring cloud base height and a Skopograph for measuring horizontal visibility.

It is therefore one object of the present invention to reconcile these conflicting requirements by providing apparatus for use at airports which are unattended, or unattended for a large portion of the time, to provide information to pilots of approaching aircraft as to horizontal and vertical visibility. Since the airports are assumed to be unattended, or at least unattended for a large portion of the time, the equipment should be capable of unattended operation, i.e. it should not require the presence of a human being to monitor, filter and/or transfer information to a pilot. Furthermore, since the equipment is destined for smaller airports, it must be relatively simple and inexpensive. In accordance with the invention, a single instrument makes both measurements. On the other hand, since the lives of pilots, as well as any passengers they carry, depends on the accuracy of information relating to vertical and horizontal visibility, the equipment must, at the same time it is inexpensive, also be accurate and capable of detecting various fault conditions.

SUMMARY OF THE INVENTION

These and other objects of the invention are met by providing apparatus for measurement of vertical and horizontal visibility, in a relatively simple and inexpensive fashion which is capable of unattended operation.

A light source is provided which emits optical energy in at least two different directions, preferably those directions are, respectively generally parallel and perpendicular to the local ground contours at an airport. A light detector is provided a distance B from the light source, in a generally horizontal direction. The light detector is mounted for rotary motion about an axis which is generally horizontal so that the field of view of the light detector is altered as a function of time. Thus, at one time the light detector may include, within its field of view, the light source, at another time the field of view is generally upwards at an angle to the horizontal which varies as a function of time.

The light source can be continuous or pulsed. A pulsing feature can be used to discriminate against background and spurious light in a known manner. Typically, pulsing rates have been in the range of about 2 per minute to about 30 per second. The source may be coherent (for example a laser) or incoherent. Desirably, average radiated power is determined by the detector characteristic and the desired range of the instrument so as to assure detectability. The limiting factor may be range of the cloud base heights, e.g. 3000 feet.

The response of the light detector at a time when its field of view includes the source provides data from which horizontal visibility can be determined. Measurement of vertical visibility depends on the reflection characteristics of a cloud layer. The height of a cloud layer can be determined by the product of the distance B (the base line between the light detector and the light source) and the tangent of the angle the light detector makes with the horizontal at a time when light emitted by the light source is reflected by the cloud base and detected by the light detector. Accordingly, horizontal and vertical visibility are determined by the response of the light detector to the light source at times when the light detector's field of view is different.

A digital processor (for example, a microprocessor) receives the response of the detector. The processor input includes the detector response as well as an indication of the angle the detector makes with some reference (for example horizontal) at the time the detector response is sampled. For calibration purposes, a fiber optic path is provided directly from source to detector, with known attenuation. The processor can disable the normal detector field of view and image the output of the fiber optic path (directly from the source) onto the detector. This provides a reference of known attenuation indicating both the output of the light source and the response of the detector.

The processor is arranged to obtain horizontal and vertical visibility measurements based on the detector response and the calibration response of the detector. In addition, and based on the angular data input, the vertical visibility and horizontal visibility input data can be separated, i.e. horizontal visibility input data is determined when the angle with the reference is at some predetermined relation (for example, zero for a horizontal reference). Furthermore, the product of the tangent of the angle of the detector with the reference and the base line (the distance between the detector and the source) at the time when light is detected by the detector indicates the vertical height of the cloud layer from which the light was reflected from the source to the detector. The processor is also capable of performing a time trend analysis on vertical and horizontal visibility so as to predict (for example, for up to 1 hour into the future) predicted parameters for vertical and horizontal visibility. The data can also be logged by the processor for historical or archival purposes.

Finally, once the data has been computed it must be communicated to the pilots of approaching aircraft. In order to effect this function automatically and without the necessity for human intervention, the processor is coupled to a conventional voice synthesizer which in turn is coupled to a radio. Based on the computed data, the processor controls a synthesizer to vocalize the computed data. This vocalized message is coupled as the modulating input to a conventional radio allowing the pilots of approaching aircraft to hear via their own radio receivers present and predicted conditions at the airport.

To prevent mis-operation due to changes in position or orientation of source and/or detector, a level sensor may be mounted at the light source providing a monitor input to the processor. In this fashion, changes in direction of the light emitted by the source can be detected. Similarly, directional alignment is monitored and changes can be detected. An input indicating position or orientation alterations can result in a signal output calling for maintenance.

Accordingly, in one aspect the invention provides an information sensing device particularly suited for unattended airports for sensing vertical and horizontal visibility, comprising:

a light source emitting optical energy in at least two directions, a light detector spaced from said light source by a distance B, in a generally horizontal direction, means supporting said light detector for motion about a general horizontal axis for altering a field of view of said light detector as a function of time, and means responsive to said light detector for determining horizontal visibility and vertical visibility by sampling a response of said light detector to said light source at different times.

BRIEF DESCRIPTION OF THE DRAWINGS

The present invention will now be described in further detail so as to enable those of ordinary skill in the art to make and use the same, when taken in conjunction with the attached drawings in which like reference characters identify identical apparatus and in which:

FIGS. 6A–6C are a flow diagram of a suitable processing routine.

DETAILED DESCRIPTION OF PREFERRED EMBODIMENTS

Figure 1:
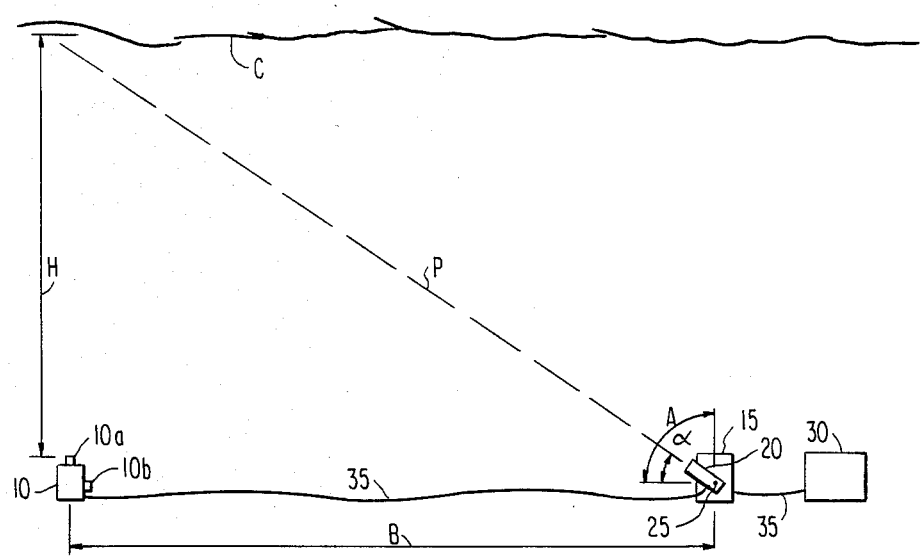
FIG. 1 illustrates the sensing equipment located at an airport.

As shown in FIG. 1, a light source 10 is provided which preferably emits optical energy, e.g. light, in two perpendicular directions via output ports 10a and 10b. For reasons which should be apparent, one of the output ports 10b outputs light in a generally horizontal direction. Spaced a distance B (or base line distance) from the light source 10 is a light detector 20. The light detector 20 may be for example a conventional photo diode, and is mounted for rotary oscillatory movement about a generally horizontal axis 25, so that the field of view of the detector 20 varies as a function of time. This motion of the detector 20 may be provided by a conventional motor or the like 15 which is provided with a shaft angle encoder or the equivalent outputting an electrical signal representative of the instantaneous angular relation between the longitudinal axis of the detector 20 and a reference such as a horizontal reference. The motor 15 provides for a total angular movement of the detector through an angle A, which for example may be 86°. As illustrated in FIG. 1, the detector makes an angle $\alpha$ with the reference and, by reason of the motor 15, the angle $\alpha$ varies as a function of time between about 0° and about 90°.

While FIG. 1 shows the light source 10 with perpendicular light emitting ports 10a and 10b and a rotating detector 20, it is within the scope of the invention to exchange the motion of source and detector. More particularly, the detector (one or two detecting elements) could have fixed field(s) of view through ports 10a and 10b while the source is swept by rotation about axis 25 by the motor 15. For purposes of a specific description, however, the source is located at 10 emitting optical energy via ports 10a and 10b with the detector's field of view rotated about axis 25 by motor 15.

For purposes of determining the height H of the base of the cloud layer C, the detector 20 relies on a reflection of light emitted from the output port 10a. The light reflected from the lower base of the cloud layer C follows a path P. Accordingly, knowing the base line distance B, and the angle which the detector makes with the horizontal reference, the height H can be computed. H=B*tan α.

Figure 2:
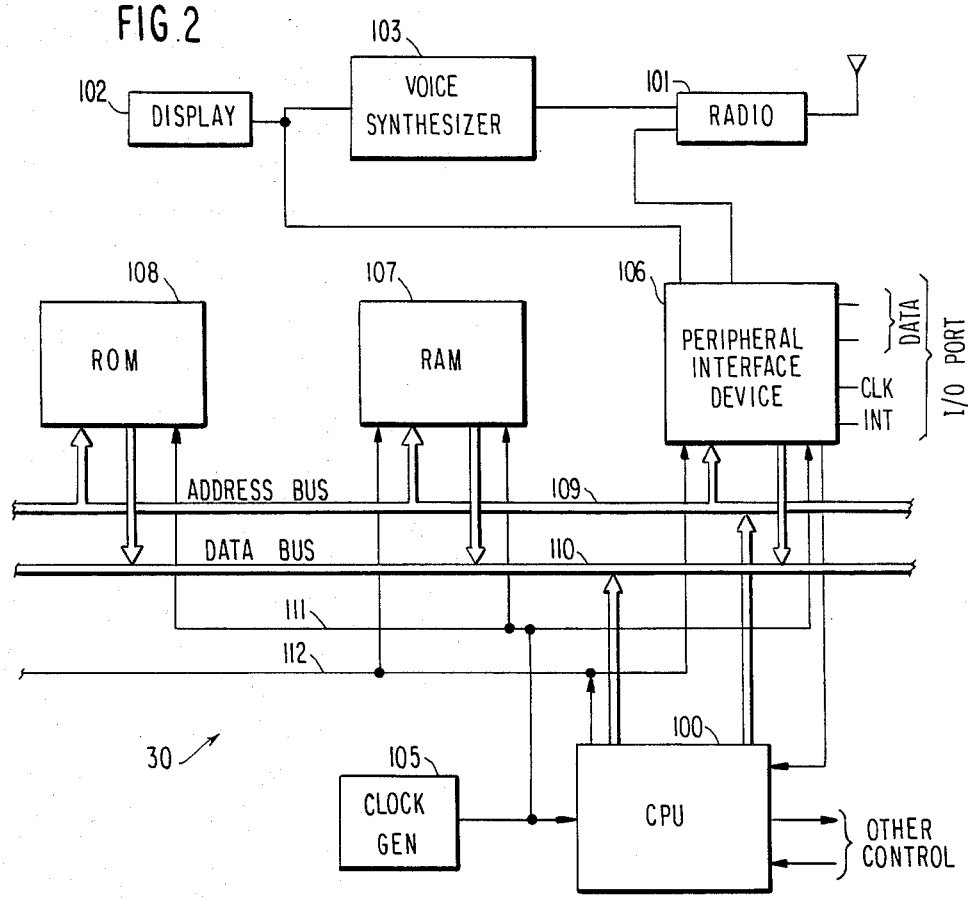
FIG. 2 is a block diagram of the electronics equipment which is provided for sampling, recording, processing and transmitting data representing horizontal and vertical visibility.

Accordingly, the light detector 20 provides a number of signals (either in analog or digital form) to the processing apparatus 30 via a cable connection 35. Those signals include the instantaneous response of the detector 20, and the instantaneous angular relation of the detector to the horizontal reference. Reference is now made to FIG. 2 to illustrate in detail the processing apparatus 30.

FIG. 2 delineates certain major features of a microprocessor. These are:
Central Processor Unit (CPU): 100
Clock Generator: 105
I/O Port: 106
Read Only Memory (ROM): 108
Random Access Memory (RAM): 107.

The CPU 100 is the heart of the microprocessor and performs a repertoire of logic functions upon binary input data. This data typically is in units or blocks 8-bits wide and is commonly referred to as a byte. The instructions and data needed by the CPU 100 are requested by the ADDRESS BUS 109. The returned information comes via the DATA BUS 110 and can result from ROM 108, RAM 107, or PERIPHERAL INTERFACE DEVICE (PID) 106. It is possible, under CPU control, for data to flow from PID 106 to RAM 107 via BUS 110 or from RAM 107 to PID 106 via BUS 110. This is a frequent occurrence when data requires additional processing.

The most usual situation is that the algorithm or program is stored in ROM 108, since it does not change. Measured data and dynamically changing values are stored in RAM 107. Sampled input is via PID 106 as are outputted values via RAM 107 to the I/O port 106.

The clock generator 105 is crystal controlled so that accurate time reference is always available. The data through the I/O port 106 is digital and external devices, such as the detector 20, may need analog to digital conversion to assure binary digital data at PID 106. Similarly, a motor may require an analog input, hence a digital to analog conversion (D/A) may be required between PID 106 and the motor. Typically, these digital interfaces are 3-state so they may be directly paralleled and read into or out of as the CPU 100 requires.

The CPU 100 under ROM 108 control can perform data manipulation as well as add, subtract, multiply, divide and combine these operations in any sequence.

Based on processing to be described hereinafter, the CPU 100 computes present horizontal and vertical visibility, and predicts future visibility. This information is coupled through a second I/O port of the peripheral interface device 106 to a voice synthesizer 103, and to a display 102. The voice synthesizer 103, based on this information vocalizes the information to a voice message and couples the voice message to the modulating input of a radio 101. Based on the presence of another control signal from the peripheral interface device 106, i.e. when a message is ready, the radio 101 is energized to output the voice message, modulated on a selected carrier. This allows the information to be detected, demodulated and understood by the pilots of approaching aircraft.

The output of the detector 20 along with the output of the shaft angle encoder associated with the motor 15 is coupled to the I/O port 106. The instantaneous output of the detector 20 can be sampled and processed and/or stored when the shaft angle encoder indicates that the field of view of the detector 20 may provide relevant information; more particularly, when the detector's field of view is in or near the port 10b, or when the angle α is in a region in which light reflection from the cloud base C can be expected. The processing performed on the instantaneous response of the detector 20 during these two different times is different and will now be explained.

When the field of view of the detector 20 is in or near the port 10b, the processing is directed at determining horizontal visibility. The detector response characteristic to the particular spectrum of optical energy is available to the microprocessor CPU 100 via ROM 108. This characteristic can represent a family of curves correlating horizontal visibility with source intensity. Derivation of source intensity will be described below. Accordingly, knowing source intensity and detector response, horizontal visibility is either directly determined from the contents of ROM 108 or interpolated therefrom.

Processing to determine the height of the cloud base C requires determination of the angle α at which a response (or maximum response) is detected travelling over the path P. To this end, for example, the microprocessor may store, in RAM 107, detector response and corresponding angle α in a given portion of the total angle A. Using well known binary search techniques, the maximum response of the detector and the corresponding angle α is readily determined. If desired, the portion of the sweep of the detector during which storage occurs can also be controlled by the CPU 100. Knowing the angle α at which the maximum detector response is obtained, the height H is readily determined by computing B*tan α.

As was mentioned above, the determination of horizontal visibility requires estimation or measurement of the intensity of the source 10. This is obtained using the known attenuation of the fiber optic channel 35. More particularly, a pair of shutters within the detector 20 are alternately opened and closed so as to image on the detector 20 either light (direct or reflected) from the source 10 via the atmosphere or light from the source 10 via the fiber optic channel 35. Since the attenuation of the fiber optic channel is predetermined, the response of the detector 20 when light is incident from the fiber optic channel 35 can be used to estimate or measure the intensity of the source 10. Accordingly, the operating routine of the microprocessor includes operation of the shutters included in the detector 20, and described in connection with FIG. 4.

At the time of installation, the source 10 and detector 20 are installed in alignment with one another, and with the port 10a oriented as shown in FIG. 1. However, since source and detector are in a relatively uncontrolled environment (at least out of doors) and since predetermined relative positioning is necessary to intended operation, the invention includes apparatus to monitor any change in the relative position and/or orientation of the source 10 and detector 20. It should be apparent that longitudinal alignment of source 10 and detector 20 is necessary. Furthermore, the port 10a should be maintained generally perpendicular to the base line B.

Figure 3:
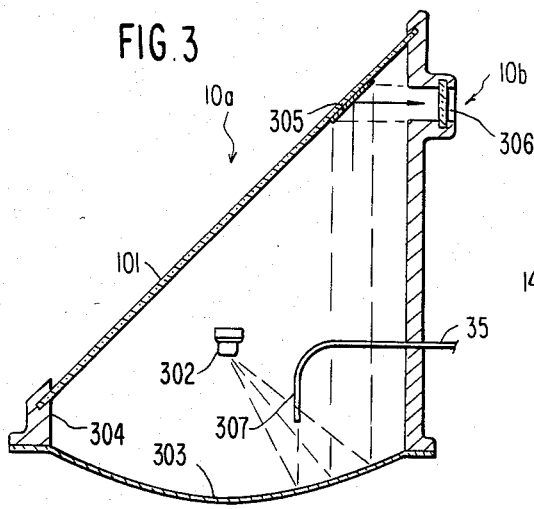
FIG. 3 is a detail of a suitable light source.

FIG. 3 is plan view of one embodiment of the source 10 with the end wall broken away to reveal the interior of the source 10. As shown, the source 10 includes a pulsed light source 302 arranged within a housing formed of side walls 304 (which can be cylindrical), a parabolic mirror 303, and a transparent rain shield 101. The rain shield 101 and mirror 303 are supported in the side walls 304, which in turn is supported by a stable base (not illustrated). The pulsed light source 302 emits in the direction of the parabolic mirror 303 which reflects the light to pass through the rain shield 301.

A horizontally directed output port 10b is formed within the side wall 304 and includes a transparent shield 306. A portion of the rain shield 301 is reflective, to form a partial reflector 305 and located, along the rain shield 301, so that light reflected from the parabolic mirror 303, which intercepts the reflector 305, exits through the transparent shield 306; this forms the output port 10b.

Finally, a support tube 307 is located within the side walls 304 to intercept light reflected from the parabolic mirror 303. The tube 307 is mated, at the side wall 304, with one end of a fiber optic light conductor 35.

Figure 4:
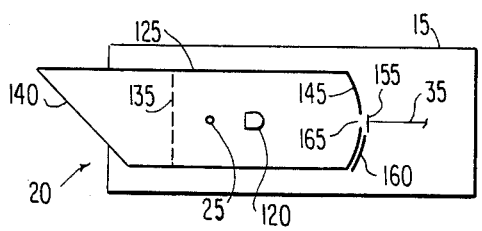
FIG. 4 is a detail of a suitable light detector.

FIG. 4 illustrates the light detector 20. More particularly, as shown in FIG. 4, a motor housing 15 supports a shaft on the axis 25 of the detector 20, for rotating the detector 20 about the axis 25. The detector 20 includes a housing including side walls 125 and a parabolic mirror 145. Light entering a transparent rain shield 140 is reflected by the mirror 145 and impinges on the photo diode 120 which is the active element of the detector 20. The light entering via the transparent rain shield 140 can be controlled by the shutter 135, so that when the shutter 135 is closed, light entering from the rain shield 140 is blocked from reaching the mirror 145.

The mirror 145 includes a small hole 165 directly adjacent to which is a second shutter 155 located between an end of the fiber optic cable 35, which is supported on the motor housing 15, and the hole 165. For light control purposes, a curved wall 160 is supported on the housing 15 so as to impede spurious light paths through the hole 165 when the detector 20 is rotated. Those skilled in the art will understand that the dimensions of the hole 165 and the shutter 155 are exaggerated in FIG. 4 over that which is necessary. The hole 165 and the shutter 155 need only be so large as to couple light from the fiber path 35.

Figure 5A:
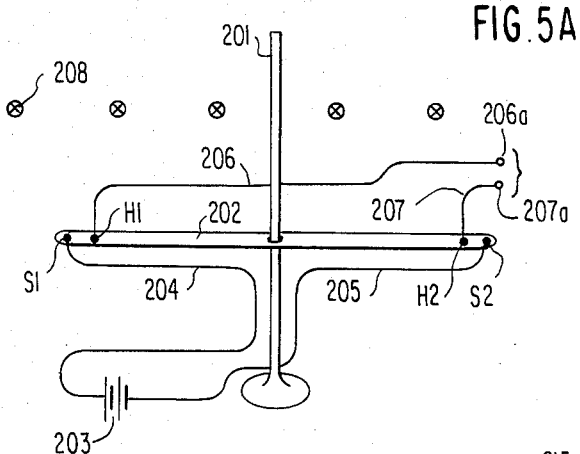
FIGS. 5A and 5B illustrate sensing devices for detecting changes in source and/or detector orientation or alignment.
Figure 5B:
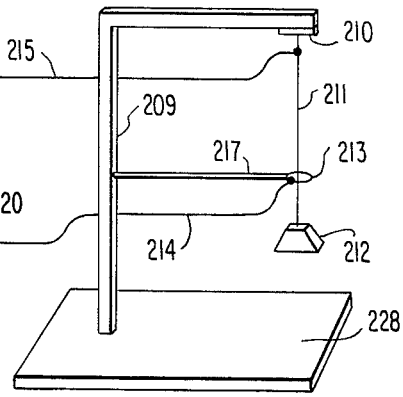

FIGS. 5A and 5B illustrate devices associated with both the source 10 and detector 20, to detect changes in alignment or orientation. Preferably, the sensors of FIGS. 5A and 5B are associated with the base of the source 10 and the base or motor 15 of the detector 20. More particularly, FIG. 5A illustrates a rotation sensor. As shown in FIG. 5A, a generally vertically extending support 201 is stably supported in the earth's magnetic field which is represented by the vectors 208 extending perpendicular to the plane of the illustration. The support 201 stably supports a Hall effect device 202 perpendicular to the magnetic field. The Hall effect device 202 has two sets of contacts, a first set of contacts S1-S2 is connected to conductors 204 and 205 which is provided with a potential difference via a potential source 203 Accordingly, a DC current flows between the contacts S1-S2.

A second set of contacts H1-H2 in the Hall effect device 202 is connected to conductors 206 and 207 which are brought to a pair of output terminals 206a and 207a. On installation the support 201 is rotated so that the Hall effect device 202 is perpendicular to the magnetic field 208. Under these circumstances, there is no potential difference across the terminals 206a, 207a. However, if the support 201 is rotated about an axis parallel to 201, the perpendicular relationship between field 208 and sensor 202 is destroyed and a potential difference is generated at the terminals 206a and 207a. The support 201 is stably fixed relative to the light source 10 and/or the detector 20, so that rotation of either light source 10 and/or detector 20 results in production of the aforementioned potential. This potential is sensed, and any variation therein is used to signal movement of the light source and/or detector 20. Alternatively, a gyroscopic-like device could be used to sense rotation.

FIG. 5B illustrates a device to determine tilting of light source 10 and/or detector 20 about a horizontal rotation axis. As shown in FIG. 5B, a support 209 is stably supported (relative to source 10 or detector 20) on a base plate 228. A conductive cable 211 is supported by the arm 209 via an insulator 210. The conductor 211 is maintained in a generally vertical orientation by the weight 212 attached at the other end of the conductor 211. The conductor 211 is threaded within a conductive washer 213 which is supported on an arm 217. A potential difference is maintained between the conductor 211 and the washer 213 by means of conductors 214 and 215 connected across a potential difference 220. A resistor 216 is located in the conductor 215. The washer 213 is arranged with an inner diameter larger than the thickness of the cable 211, but just slightly larger. On installation, the length of the arm 217 is arranged so that the cable 211 does not make contact with the washer 213. Under those circumstances, there is an open circuit and no current flows in the conductors 214, 215. However, if the arm 209 is tilted relative to the horizontal, then the cable 211 will make contact with the conductor 213 providing a closed circuit path for the flow of current in the conductors 214, 215. Current flow in the conductor 215 will develop a potential difference across the resistor 216. This potential difference will be reflected at the output terminals 218, 219. Sensing the potential difference across the terminals 218, 219 can be used to detect the tilting of the arm 209. The arm 209 is arranged to be stably supported relative to the detector 20 and/or the light source 10, so that tilting of the light source 10 and/or the detector 20 about a horizontal rotation axis results in tilting of the arm 209 and the production of the aforementioned potential difference.

While the apparatus shown in FIGS. 5A and 5B will reliably detect either rotation and/or tilting, those skilled in the art will understand that the invention is not limited to use of these specific devices.

Figure 6A:
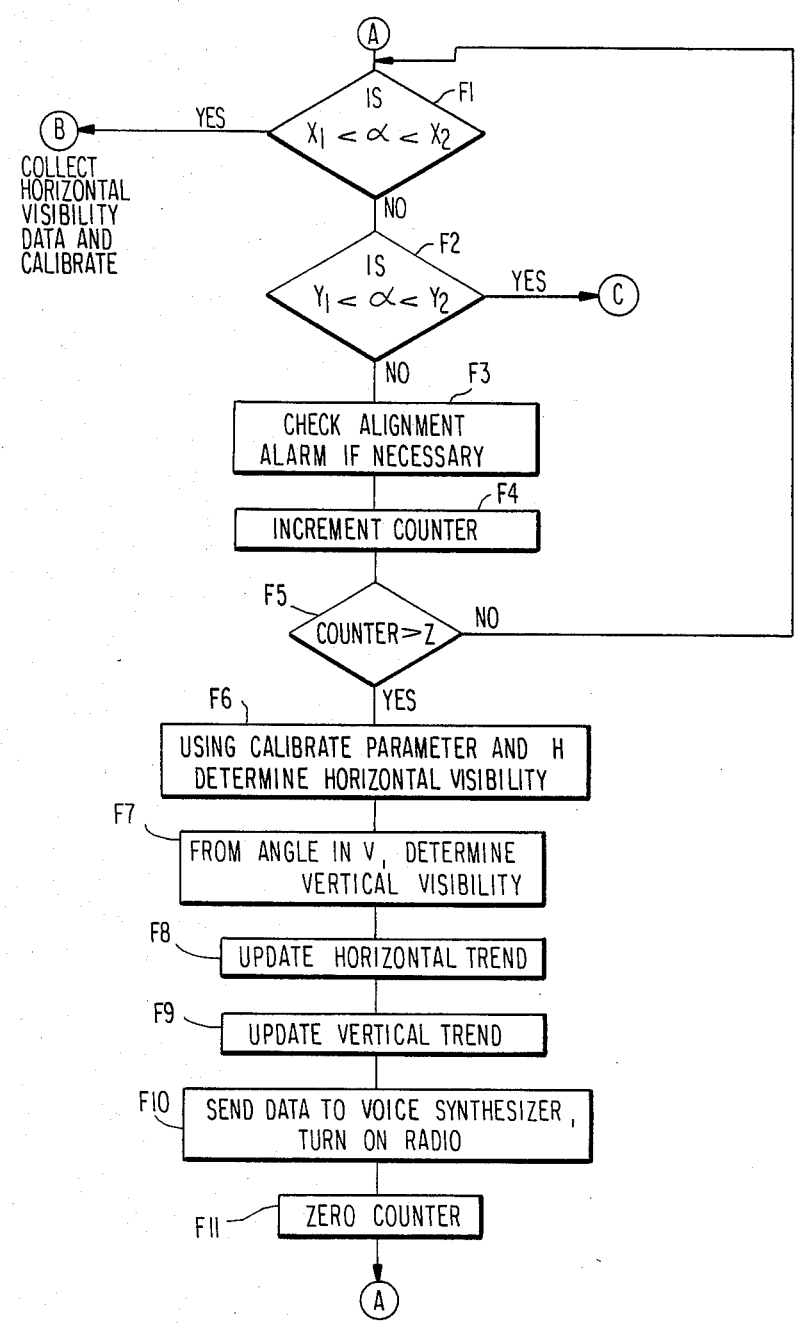

FIGS. 6A-6C illustrate one example of a processing routine which can be effected by the CPU 100 in order to derive vertical and horizontal visibility employing the apparatus shown in FIGS. 1-4, 5A and 5B. It should be understood, however, that the processing routine illustrated in FIGS. 6A-6C is but one example of many different processing routines which will perform the required functions. In determining a processing routine, several choices have to be made. The basic function of the device is to determine horizontal visibility by the response of the detector 20 to the light source 10, determine vertical visibility (or more properly, an indication of the lowest extent of the cloud base), to calibrate these measurements using the mean attenuation of the fiber optic test channel 35, and to ensure that after installation, the light source and detector are not subject to tilting and/or misalignment.

From the preceding description, it should be apparent that the field of the view of the light detector 20 is swept in a reciprocating or cyclical fashion through a predetermined arc, and only during a small portion of the time will useful measurements be effected. Those useful portions of the sweep occur at two distinct instants, first when the longitudinal axis of the detector 20 is in or near horizontal (and at this time, horizontal visibility can be measured) and when the longitudinal axis of the detector 20 makes an appropriate angle with the horizontal to detect light reflected from the cloud base via the path P (see FIG. 1). The first of these instants can be predetermined, the second will vary as the cloud base height changes. Therefore, the processing routine should admit of varying the angle at which vertical visibility is measured. The processing routines described in FIGS. 6A-6C provide for this flexibility. In addition, for calibration purposes, the shutters must be operated so that the detector response from light transmitted over fiber optic channel 35 can be measured. Preferably, the detector and/or the fiber optic cable 35 is oriented so that the detector 120 can view the fiber optic cable at a time when the longitudinal axis of the detector 20 makes an angle with the horizontal at which no light from the source 10 would be expected at the detector 20. For example, such an angle could be either a few degrees above or below the horizontal.

The motor 15 could be arranged to continuously sweep the detector 20, and measurements could be taken at predetermined times in this sweep. On the other hand, it is also within the scope of the invention to command the motor to sweep the detector 20 at discrete times, separated by times during which the detector 20 is at rest. The processing routine shown in FIGS. 6A-6C assumes that the detector 20 is continuously in motion. In addition, the sampling of the detector 20 effected by the processing routine shown in FIGS. 6A-6C occurs only at specified points in the sweep, those skilled in the art will be aware that an acceptable alternative is to sample the output of the detector 20 continuously while simultaneously recording the output of the shaft angle encoder, and process this data to derive both horizontal and visibility.

The processing to be described is broken down into three main components, i.e. an output routine which performs the determination of horizontal and vertical visibility as well as performing trend calculations, along with the output functions. Two branches from this routine provide, firstly for collection of horizontal visibility data and calibration data, and secondly for collection of vertical visibility data. Referring now to FIG. 6A, it will be seen that the processing is arranged in an endless loop. Both the detector response and the shaft angle encoder output is continuously available at the peripheral interface device 106. Function F1 compares the shaft angle encoded output with predetermined quantities $X_1$ and $X_2$. When the angle of the detector lies between $X_1$ and $X_2$, horitonal visibility and calibration functions are being performed. Assuming that the shaft angle encoder is not within its range, then function F2 determines if the shaft angle is between $Y_1$ and $Y_2$. These parameters determine the look angle at which vertical visibility data will be taken, and as will become clear hereinafter, the parameters are adjustable based on the data received. Assuming that the shaft angle is not within this point, then function F3 checks alignment. Outputs from the tilting and rotation sensors in both source and detector are brought back to the peripheral interface device 106, and function F3 merely checks to see that the pattern of these outputs is as expected. Any variation in the expected pattern produces an alarm.

Function F4 increments a counter. Although data is continuously taken, measurements and computations only occur periodically, on overflow of the counter. The counter value Z is sufficient to allow processing F6 through F10 with counter zeroed at F11. Therefore, function F5 checks to see if the counter has overflowed, and if it has not, processing loops back to function F1. On the other hand, if the counter has overflowed, then function F6 is performed. As previously mentioned, horizontal visibility can be determined from the response of the detector 120 and the calibration parameter. Function F6 uses these parameters to determine horizontal visibility. Derivation of the parameters will be described in connection with FIG. 6B. Function F7 then uses the angle in a register V to determine vertical visibility (i.e. base of the cloud layer C). Functions F8 and F9 update the horizontal and vertical visibility trends. Trend analysis is well known to those skilled in the art; for example, future horizontal or vertical visibility can be determined by noting the most recent rate of change and projecting the parameter into the future. Finally, F10 sends the computed data, i.e. horizontal and vertical visibility, horizontal and vertical visibility trends, to the voice synthesizer and enables the radio. The voice synthesizer vocalizes the data coupled from the peripheral interface device 106 and passes on the vocalized message to the radio where it is modulated on a carrier for transmission. Finally, function F11 zeros the counter and returns to point A.

If in the course of processing functions F1-F11 in FIG. 6A, function F1 determines that the angle is within the range for collecting horizontal visibility data and calibration purposes, then function F12 is performed. Function F12 reads and stores the detector and encoder outputs in a H stack. Function F13 determines if the detector is still within the appropriate angular range, and if it is, function F12 is again performed, and this loop is repeatedly performed to build up detector response and encoder output data. When the detector angle is no longer within the appropriate range, function F14 is performed to locate the maximum detector response in the stack H and stored in a register H.

Thereafter, function F14 is performed to determine if the angle of the detector is within a different range, that is, between $X_3$ and $X_4$. Between this angular range, calibration operation is effected. If the angle is not within this range, then processing loops back to point A (FIG. 6A).

However, assuming that the angle is within the calibration range, then function F16 reverses the shutter condition. Referring briefly to FIG. 4, it illustrates that the detector 20 includes a pair of shutters 135, 155. During normal operation, the shutter 135 is open and the shutter 155 is closed. Function F16 reverses this condition, i.e. closes shutter 135 and opens shutter 155. In this condition, the light detector 120 is no longer responsive to light entering the rain shield 140, but rather, now includes the end of the fiber optic cable 35 in its field of view via the open shutter 155 and the hole 165. Accordingly, function F17 now reads the detector response and stores this as a calibrate parameter. This calibrate parameter can be used to normalize the response of the detector to horizontal and vertical visibility. Function F18 then reverses the shutter condition so that, following function F18, shutter 135 is again open and shutter 155 is again closed. Calibration having now been performed, processing loops back to point A (FIG. 6A).

In the event that the angle of the detector is within $Y_1$ and $Y_2$, then processing skips to point C (FIG. 6C) to effect vertical visibility measurements. Function F20 reads and stores the detector response and the encoder output in a VS stack. Function F21 determines if the angle at the detector is still within the appropriate range, if it is, function F20 is again performed. The loop of functions F20 and F21 are performed so long as the detector is within the appropriate angular range. When the detector leaves this range, function F22 locates the maximum detector response in the VS stack. The corresponding encoder word is withdrawn from the VS stack and written in the V register. This parameter will be used, in function F7 to determine vertical visibility. Thereafter, function F23 updates the limits $Y_1$ and $Y_2$. More particularly, the detector response stored in the VS stack will, as a function of angle (or encoder output), increase, level off and then decrease. If the initial range $Y_1$, $Y_2$ is still valid, the peak detector response will lie generally within the middle of the range. However, if the cloud base height has increased or decreased, then the peak will be skewed toward one end of the range or the other. Function F23 corrects the range to maintain the peak approximately mid-range. In this fashion, the vertical visibility measuring range tracks changes in cloud height.

It is recognized that under certain ground fog conditions, the detector 20 response will decrease initially while scanning out of the top of the ground fog layer and subsequently increase, plateau and decrease as previously described for the lowest cloud layer. The lowest value of $Y_1$ can be limited to a value that corresponds to the upper limit of a local ground fog condition. For example, 50 foot top of fog and 500 foot separation corresponds to 5.71 degrees. A detected but decreasng response at 5.71 degrees will correlate with a diminished horizontal visibility and if so, then the unit warns of ground fog and proceeds to detect the bottom of the cloud layer as previously described.

I claim:

1. An information sensing device particularly suited for unattended airports for sensing vertical and horizontal visibility, comprising:
a light source emitting optical energy in at least two directions,
a light detector spaced from said light source by a distance B, in a generally horizontal direction,
means rotating said light detector about a generally horizontal axis for altering a field of view of said light detector as a function of time, and
control means responsive to said light detector for determing horizontal visibility and vertical visibility by sampling a response of said light detector to said light source at different times and fields of view and producing representations thereof.

2. The apparatus of claim 1 in which said control means measures horizontal visibility by sampling said light detector response when said source is within a field of view of said light detector.

3. The apparatus of claim 1 in which said control means measures vertical visibility from an angular position of said light detector at which optical energy emitted by said source is reflected by a cloud base.

4. The apparatus of any of claims 1-3 in which said light detector includes:
means for producing a detectable condition in response to rotation of said light detector about a vertical axis.

5. The apparatus of claim 4 in which said light detector further includes:
means for producing a detectable condition in response to rotation about any horizontal axis.

6. The apparatus of any of claims 1-3 in which said light source includes:
means for producing a detectable condition in response to rotation of said light source about a vertical axis.

7. The apparatus of claim 6 in which said light source further includes:
means for producing a detectable condition in response to rotation of said light source about any horizontal axis.

8. The apparatus of any of claims 1-3 in which:
said control means includes time trend analysis means for determining rate of change of horizontal and vertical visibility and for producing representations of future horizontal and vertical visibility.

9. The apparatus of claim 8 which includes:
a voice synthesizer, and
means coupling representations of horizontal and vertical visibility and future horizontal and vertical visibility to said voice synthesizer.

10. The apparatus of claim 9 which further includes a radio transmitter coupled to said voice synthesizer.

11. The apparatus of claim 4 in which said control means includes alarm means responsive to said detectable condition for initiating an alarm.

12. The apparatus of claim 7 in which said control means includes alarm means responsive to said detectable condition for initiating an alarm.

13. The apparatus of any of claims 1-3 which further includes:
a fiber optic reference light path between said light source and said light detector and wherein:
said control means includes means for calibrating light detector response to said light source.

14. The apparatus of claim 13 which further includes:
shutter means with two conditions adjacent said detector means for controlling a field of view of said detector means between only said fiber optic reference light path in one said condition and excluding said fiber optic reference light path in another of said conditions and
wherein said control means includes shutter control means for controlling said shutter means conditions.

* * * * *